United States Patent
Deck et al.

(10) Patent No.: US 8,672,963 B2
(45) Date of Patent: Mar. 18, 2014

(54) LANCET DEVICE

(75) Inventors: Frank Deck, Niederkirchen (DE);
Christian Hoerauf, Oftersheim (DE);
Malte Hinrichs, Berlin (DE); Hartmut Berg, Malente (DE); Torsten Grunwald, Malente (DE); Mathias Jotter, Eutin (DE); Manfred Rufer, Bosau (DE); Jens Storjohann, Hamburg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 936 days.

(21) Appl. No.: 12/013,057

(22) Filed: Jan. 11, 2008

(65) Prior Publication Data

US 2008/0188883 A1    Aug. 7, 2008

Related U.S. Application Data

(63) Continuation of application No. PCT/EP2006/005929, filed on Jun. 21, 2006.

(30) Foreign Application Priority Data

Jul. 13, 2005   (EP) .................................... 05015171
Mar. 3, 2006   (EP) .................................... 06004319

(51) Int. Cl.
*A61B 17/14*   (2006.01)
*A61B 17/32*   (2006.01)

(52) U.S. Cl.
USPC ........................................................ 606/182

(58) Field of Classification Search
USPC ......... 606/167, 169, 171, 181, 182, 183, 185;
600/583; 604/22; 335/76, 171, 179,
335/220, 229–235, 251, 266
See application file for complete search history.

(56) References Cited

U.S. PATENT DOCUMENTS 3,051,173 A  *  8/1962  Johnson et al. ............... 604/152
3,805,795 A  *  4/1974  Denniston et al. ................ 607/6
(Continued)

FOREIGN PATENT DOCUMENTS

EP     1 063 666 A2    12/2000
JP     H02-095352       4/1990
(Continued)

OTHER PUBLICATIONS

Koichi et al. Machine translation of JP 2003-339680 A. Published Feb. 12, 2003.*

(Continued)

*Primary Examiner* — Ryan Severson
*Assistant Examiner* — Katherine M Shi
(74) *Attorney, Agent, or Firm* — Woodard, Emhardt, Moriarty, McNett & Henry LLP

(57) ABSTRACT

The present invention relates to a lancet device, by which a lancet can be displaced along a piercing path for generating a piercing wound in a skin surface, in particular to obtain bodily fluid for diagnostic purposes, comprising a lancet drive having drive means to generate a drive force for a piercing movement of the lancet along the piercing path in the direction toward the skin surface. According to the present invention, the lancet drive comprises a magnet, by which a magnetic retention force oriented opposite to the drive force may be generated, and the lancet drive also comprises triggering means, by which the retention force may be reduced enough that the lancet is accelerated in the direction toward the skin surface under the effect of the drive force generated by the drive means. The present invention also relates to a method for generating a piercing wound, in which the drive spring is held in a tensioned state using a magnetic retention force oriented opposite to the drive force before the triggering of a piercing wound.

14 Claims, 3 Drawing Sheets

(56) References Cited

U.S. PATENT DOCUMENTS

| | | | |
|---|---|---|---|
| 3,832,776 A * | 9/1974 | Sawyer | 30/272.1 |
| 3,840,088 A | 10/1974 | Marumo et al. | |
| 6,037,851 A * | 3/2000 | Gramann et al. | 335/228 |
| 6,080,172 A | 6/2000 | Fujiwara | |
| 6,265,957 B1 | 7/2001 | Baginski et al. | |
| 6,364,889 B1 | 4/2002 | Kheiri et al. | |
| 6,646,529 B1 | 11/2003 | Kahnert | |
| 6,741,151 B1 * | 5/2004 | Livshitz et al. | 335/222 |
| 6,938,506 B2 * | 9/2005 | Henry et al. | 73/866.5 |
| 2002/0075109 A1 * | 6/2002 | Iwazaki | 335/220 |
| 2003/0058667 A1 * | 3/2003 | Suzuki et al. | 363/59 |
| 2004/0049219 A1 | 3/2004 | Briggs et al. | |
| 2004/0155743 A1 | 8/2004 | Sako | |
| 2004/0219192 A1 * | 11/2004 | Horstmann et al. | 424/449 |

FOREIGN PATENT DOCUMENTS

| | | |
|---|---|---|
| JP | H02-095352 A | 4/1990 |
| JP | 2003-339680 | 12/2003 |
| JP | 2003-339680 A | 12/2003 |
| WO | WO 02/100460 A2 | 12/2002 |

OTHER PUBLICATIONS

International Patent Application PCT/EP2006/05929 International Search Report mailed Nov. 20, 2006.

International Application PCT/EP2006/005929, "International Preliminary Report on Patentability," mailed May 27, 2008 (translation).

* cited by examiner

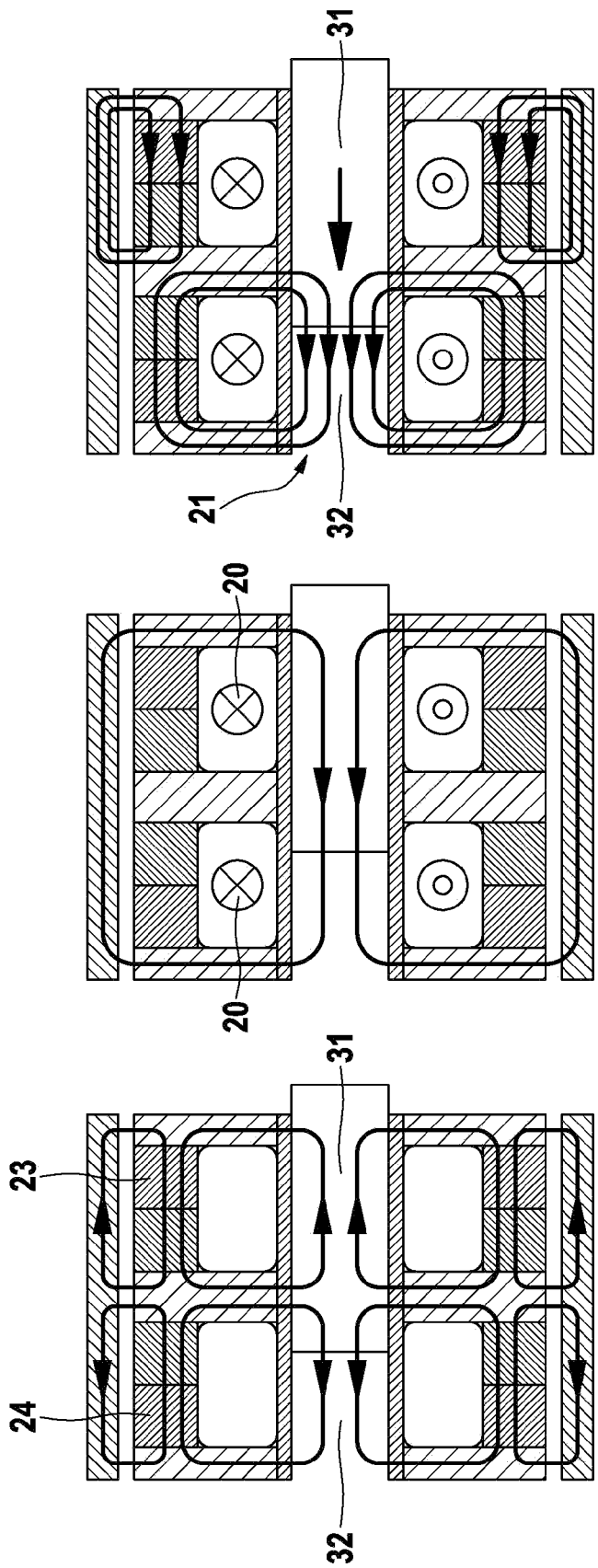

LANCET DEVICE

CROSS-REFERENCE TO RELATED APPLICATION

This application is a continuation of International Patent Application No. PCT/EP2006/005929 filed Jun. 21, 2006, which claims the benefit of European Patent Application No. 06 004 319.7 filed Mar. 3, 2006 and of European Patent Application No. 05 015 171.1 filed Jul. 13, 2005, which are all hereby incorporated by reference in their entirety.

BACKGROUND

The present invention relates to a lancet device, by which a lancet can be displaced along a piercing path to generate a piercing wound in a skin surface, in particular to obtain bodily fluid for diagnostic purposes, comprising a lancet drive having drive means for generating a drive force for a piercing movement of the lancet along the piercing path in the direction toward the skin surface.

Furthermore, the present invention relates to a method for generating a piercing wound in a skin surface using a lancet, in which the lancet is accelerated along a piercing path using a drive force generated by a drive spring in the direction toward the skin surface.

Lancet devices are required, for example, by diabetics, who have to check their blood sugar level frequently to be able to keep it within specific setpoint limits by insulin injections. Extensive scientific experimentation has proven that a dramatic reduction of the most severe long-term complications of diabetes mellitus (such as retinopathy with resulting blinding of the patient) may be achieved using an intensive treatment having at least four analyses per day.

For users of lancet devices, on one hand the most low-pain piercing possible and on the other hand the simplest possible operation and ability to handle the lancet device used are of great significance.

A requirement for low-pain piercing is the most rapid possible piercing movement having a short dwell time of the lancet in the skin. The use of drive springs has proven itself in the prior art for a correspondingly strong acceleration of the lancets. A disadvantage of lancet devices of this type is that manually tensioning the drive springs after completed piercing is cumbersome for many users. This is true in particular for people whose manual dexterity is restricted by age or illness.

A lancet device in which the drive spring is automatically tensioned by an electric motor does offer increased user comfort in this regard, but has the disadvantage of being larger and heavier because of the electric motor. A lancet device having an integrated electric motor therefore represents a burden for the user, who has to carry it around continuously for frequent measurements. In addition, the production costs are significantly increased by an electric motor.

Furthermore, lancet devices are known in the prior art in which the drive force is generated electromagnetically using a coil. Lancet devices of this type are disclosed, for example, in WO 02/100460 A2 and U.S. Pat. No. 6,364,889 B1. To be able to cause a sufficiently rapid piercing movement for a low-pain piercing using electromagnetic lancet drives of this type, strong magnetic fields must be generated. This requires that relatively strong electric currents flow through the drive coils used, which may be generated not at all or only with great effort in a small, compact handheld device. Electromagnetic lancet drives have therefore not been able to succeed against mechanical drives having drive springs up to this point.

SUMMARY

The object of the present invention is to show a cost-effective way in which, in a lancet device of the type cited at the beginning, having a compact design, a sufficiently rapid piercing movement for a low-pain piercing may be generated and the user may be relieved as much as possible from preparatory handling, such as tensioning a drive spring.

This object is achieved according to the present invention using a lancet device of the type cited at the beginning in that the lancet drive comprises a magnet, by which a magnetic retention force oriented opposite to the drive force may be generated, and the lancet drive also comprises trigger means, by which the retention force may be reduced enough that the lancet is accelerated in the direction toward the skin surface under the effect of the drive force generated by the drive means.

A drive spring may be used as the drive means, which may be held in a tensioned state by the magnetic retention force. In a lancet device according to the present invention, the lancet may be retracted into its starting position via the magnetic retention force after the penetration into the skin surface. The retention force may be generated using an electromagnetic, for example, or—preferably—originate from a permanent magnet. If a permanent magnet is used, it is advantageous if the trigger means comprise a coil, by which a magnetic field may be generated, which at least partially, preferably completely compensates for the retention force of the permanent magnet. Through suitable dimensioning of the permanent magnet and the coil, the retention force generated by the magnet may be sufficiently great to cause renewed tensioning of the drive spring after completed piercing.

A lancet device according to the present invention having a drive spring has the advantage that it may be manufactured significantly more cost-effectively and compact than a lancet device having an electric motor, and nonetheless allows automatic tensioning of the drive spring.

Furthermore, a coil may be used as the drive means for a lancet device according to the present invention, to generate the drive force magnetically. The coil may also be used as the triggering means, using which the magnetic retention force is overcompensated for. The magnetic retention force is preferably generated by a permanent magnet, to which a further permanent magnet is assigned as the second part of the drive means as a drive magnet having reversed polarization, so that the magnetic fields of the permanent magnets are destructively superimposed. In this way, the drive force generated by the drive magnet is compensated for by the permanent magnet generating the retention force, so that no resulting drive force and therefore also no lancet movement results without coil current. If a current flows through the drive coil, the magnetic field of the drive magnet is superimposed constructively on the magnetic field of the coil, so that a resulting drive force to accelerate a lancet arises.

Even if the two permanent magnets compensate for one another exactly, a greater drive force may surprisingly be generated by the use of a drive coil in combination with oppositely polarized permanent magnets than using a drive coil alone. By superimposing the coil field with the fields of the oppositely polarized permanent magnets, an increased magnetic field strength results locally in a first area and a locally reduced field strength results in a second area. The locally increased magnetic field strength may be used for the purpose of magnetizing a drive element, such as a soft-magnetic coil core. The force exerted by the magnetic field on the drive element is overall greater because of the locally increased field strength than if a coil is used without permanent magnets. An important aspect of the present invention, which may also be significant independently, therefore relates to a lancet device comprising a lancet drive having:

- a first and a second magnetic field source, which generate two magnetic fields destructively superimposed in a drive chamber in operation,
- a third magnetic field source, which generates a further magnetic field in operation, which is superimposed constructively with the magnetic field of the first magnetic field source and destructively with the magnetic field of the second magnetic field source in the drive chamber, at least one of the three magnetic field sources being a permanent magnet and at least one of the three magnetic field sources being a coil, and
- a drive element in the form of a soft-magnetic coil core, which is movable back and forth between a first position and a second position in the drive chamber, to cause a piercing and retraction movement by coupling with a lancet, the magnetization of the coil core being determined by the third magnetic field source, so that the coil core is movable by a coil current from the first position into the second position and is movable back into the first position by reversing the direction of the coil current.

The object of the present invention is also achieved by a method of the type cited at the beginning according to the present invention in that the drive spring is held in a tensioned state before the triggering of a piercing movement using a magnetic retention force oriented opposite to the drive force, and the retention force is reduced enough to trigger a piercing movement that the drive spring relaxes and the lancet is accelerated in the direction toward the skin surface under the effect of the drive force generated by the drive spring.

BRIEF DESCRIPTION OF THE DRAWINGS

The present invention is explained in greater detail in the following on the basis of exemplary embodiments illustrated in the figures. The special features illustrated therein may be used individually or in combination to provide preferred designs of the present invention.

FIG. 5 shows the field course of the magnetic fields generated by the permanent magnets of the lancet drive shown in FIG. 4;

FIG. 6 shows the field course of the magnetic field generated in operation by the coil windings of the lancet drive shown in FIG. 4, and FIG. 7 shows the course of the overall field which results by superposition of the magnetic field shown in FIGS. 5 and 6.

DETAILED DESCRIPTION OF SELECTED EMBODIMENTS

Figure 1:
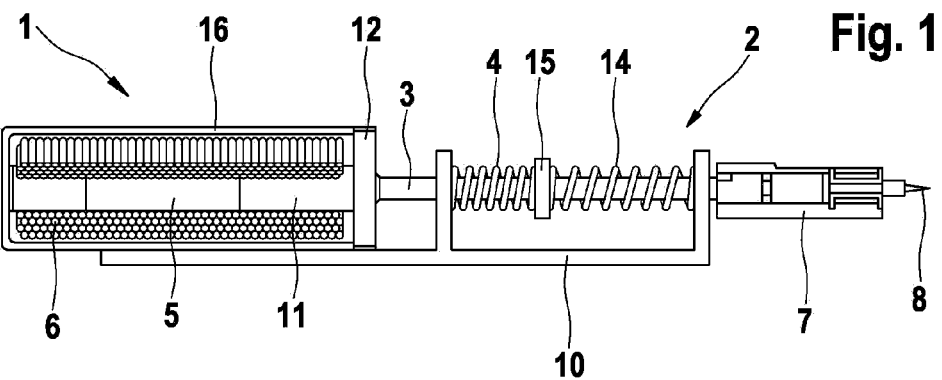
FIG. 1 shows an exemplary embodiment of a lancet device according to the present invention having tensioned drive spring.
Figure 2:
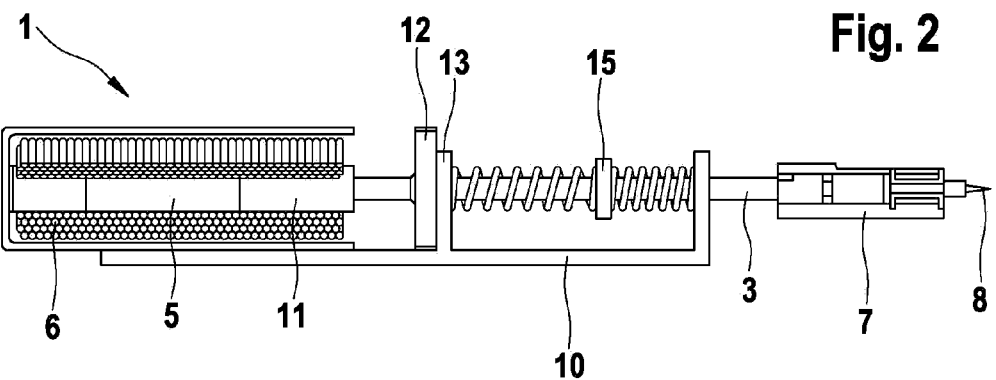
FIG. 2 shows the exemplary embodiment shown in FIG. 1 having relaxed drive spring.
Figure 3:
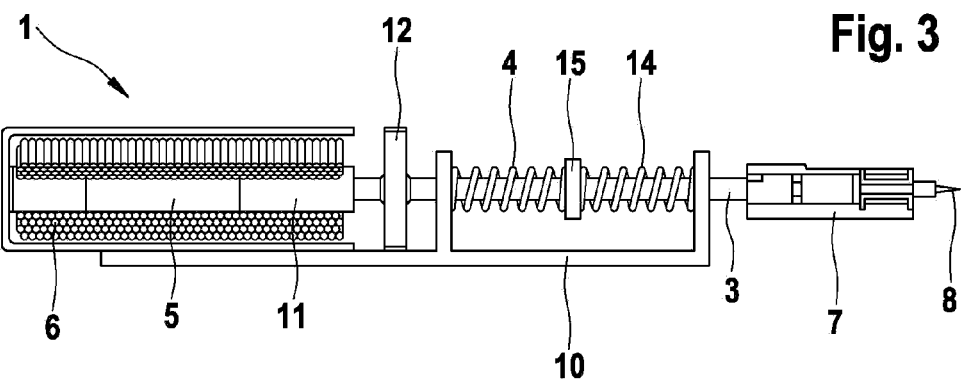
FIG. 3 shows the exemplary embodiment shown in a further illustration.

The lancet device illustrated in FIGS. 1 through 3 may be integrated in a handheld analysis device, for example, which has a measuring apparatus for assaying bodily fluid, which is obtained from a generated piercing wound. The lancet device may also be installed in a separate device as a puncture aid.

The central component of the lancet device 1 shown is a lancet drive 2, which comprises a pushrod 3, drive means in the form of a drive spring 4, a coil 6, and a permanent magnet 5 situated axially in the coil 6. The pushrod 3 carries a lancet holder 7 having a replaceable lancet 8 and is accelerated along a piercing path predefined by the guide 10 using the drive spring 4, which is implemented as a coiled spring, to generate a piercing wound.

The pushrod 3 is shown in its rest position having tensioned drive spring 4 in FIG. 1. The pushrod 3 is held in this position by the magnetic retention force of the permanent magnet 5 integrated in the coil core 11 of the coil 6. The coil core 11 having the permanent magnet 5 is situated fixed in relation to the coil 6. The coil 6 is used as the triggering means for triggering a piercing movement. A magnetic field is generated by causing an electric current to flow through the coil 6, which compensates for the retention force of the permanent magnet 5, so that the drive spring 4 relaxes and the pushrod 3 having the lancet 8 is accelerated in the direction toward the skin surface under the effect of the drive force thus generated by the drive spring 4.

The pushrod 3 is preferably made of plastic and carries an armature plate 12 made of iron or another ferromagnetic material, using which a magnetic circuit, which contains the permanent magnet 5 and a pole shoe 16 enclosing the coil 6, is closed in the position shown in FIG. 1.

The armature plate 12 may also be implemented as a permanent magnet, so that it may not only be attracted by the permanent magnet 5, but rather may also be repelled and additionally accelerated by a magnetic field generated by the coil.

A comparison of FIGS. 1 and 2 shows that the pushrod 3 has a section projecting into the coil core 11 in the rest position. Improved guiding is achieved in this way.

FIG. 2 shows the lancet device 1 having the pushrod 3 in the piercing position. In the piercing position, a stop formed by the armature plate 12 presses against a delimitation element 13 of the guide 10, so that the piercing path is delimited.

In addition to the drive spring 6, the lancet drive 2 also comprises a restoring spring 14 for generating a retraction movement of the lancet 8. The drive spring 4 is tensioned again by the retraction movement. Drive spring 4 and restoring spring 14 are each implemented as coiled springs which enclose the pushrod 3. The drive spring 4 and the restoring spring 14 are each supported at one end on a support section 15 of the pushrod 3, which is implemented as a thickened part in the exemplary embodiment shown, and at the particular other end on the guide 10. The drive spring 4 and the restoring spring 14 are situated in such a way that relaxation of the drive spring 4 causes tensioning of the restoring spring 14 and relaxation of the restoring spring 14 causes tensioning of the drive spring 4.

The term "tensioning" is to be understood in this context to mean that energy is stored in the particular effective spring. This may be caused by compression in a compression spring and by stretching in an expansion spring.

Of course, friction forces occur in the lancet device 1 shown, so that the energy stored in the restoring spring 14 in the piercing position shown in FIG. 2 is not entirely sufficient for tensioning the drive spring 4 again. In the illustrated device, the restoring spring 14 is therefore supported by the permanent magnet 5 during the retraction movement of the pushrod 3. The retention force generated by the permanent magnet 5 and the spring force provided by the restoring spring 14 are sufficient with an appropriate design of the permanent magnet 5 to bring the pushrod 3 back into the rest position shown in FIG. 1 and tension the drive spring 4. By suitable shaping of the ends of the pole shoe 16, for example, by beveling the ends, the force-distance characteristic of the retention force generated by the permanent magnet may be influenced and the retraction movement may additionally be supported.

In order that the retention force of the permanent magnet 5 may be used for tensioning the drive spring 4 again, it is sufficient to turn off the current which is sent through the coil 6 to trigger a piercing. As soon as current no longer flows through the coil 6, a magnetic field is also no longer generated by the coil 6, so that the retention force of the permanent magnet 5 is no longer compensated for and is added to the spring force of the restoring spring 14.

A piercing and retraction movement of the lancet typically lasts a total of 4 ms to 6 ms. In order that the retention force of the permanent magnet may be used for tensioning the drive spring again, the current which is sent through the coil 6 to trigger a piercing is therefore preferably turned off after 1 ms to 3 ms, preferably 1.5 ms to 2.5 ms. A current pulse having the steepest possible flanks, ideally having a rectangular profile, is especially well suitable.

An appropriately strong drive spring 4 and an appropriately strong permanent magnet 5, such as a rare earth magnet, are preferable for the most rapid possible piercing movement. To compensate for the magnetic retention force, voltages and/or current strengths which greatly exceed the performance capability of commercially available batteries are therefore preferably used. The coil 6 is therefore preferably connected via a current buffer and/or a voltage converter to an internal current source of the lancet device, such as a battery, so that a current pulse capable of compensating for the magnetic retention force may be generated using commercially available batteries. For example, capacitors or accumulators, in particular lithium-polymer accumulators, are suitable as the current buffer. Suitable voltage converters are available as DC/DC converters. The corresponding technology for generating intensive current pulses is typical in photographic apparatus for generating light flashes, for example, and may be used for the described lancet device.

To additionally support the retraction movement, the direction of the current flowing through the coil 6 to trigger a piercing may be reversed in polarity, so that the magnetic field generated by the coil 6 is added to the retention force of the permanent magnet 5. For example, a control unit having an H bridge may be used for reversing the polarity of the current. Ideally, the polarity is reversed at the moment in which the lancet has reached the outermost point of the piercing path.

A further possibility for moving the pushrod 3 from an intermediate position shown in FIG. 3 back into the rest position in case of malfunction is to excite a mechanical oscillation of the mechanical system formed by the drive spring 4, the restoring spring 14, and the pushrod 3 by periodic current surges. Upon continued excitation at the resonance frequency of this system, the amplitudes of this oscillation increase until the pushrod 3 returns into the rest position and may be held there by the retention force of the permanent magnet 5.

It may be established by a measurement of the inductance of the coil 6 whether the armature plate 12 presses against the pole shoe 16. In this way, it may thus be ascertained whether or not the pushrod 3 is located in the rest position shown in FIG. 1. The inductance of the coil 6 is preferably measured shortly after a piercing, for example, 1 to 2 seconds after a piercing. If it is established that the pushrod 3 is not located in the rest position, a mechanical oscillation of the mechanical system formed by the drive spring 4, the restoring spring 14, and the pushrod 3 is excited by periodic current surges, so that the pushrod 3 returns into its rest position.

In this way, the coil 6 is used as a position sensor for the position of the pushrod 3. The illustrated lancet device may alternatively or additionally also be equipped with other position sensors, so that the optimal instant for turning off or reversing the polarity of the current through the coil 6 may be ascertained as a function of the instantaneous position of the pushrod 3. The use of sensors therefore allows, instead of simple control of the coil current, in which a predefined profile is predefined for a current pulse, regulation of the coil current as a function of the position of the pushrod 3.

Figure 4:
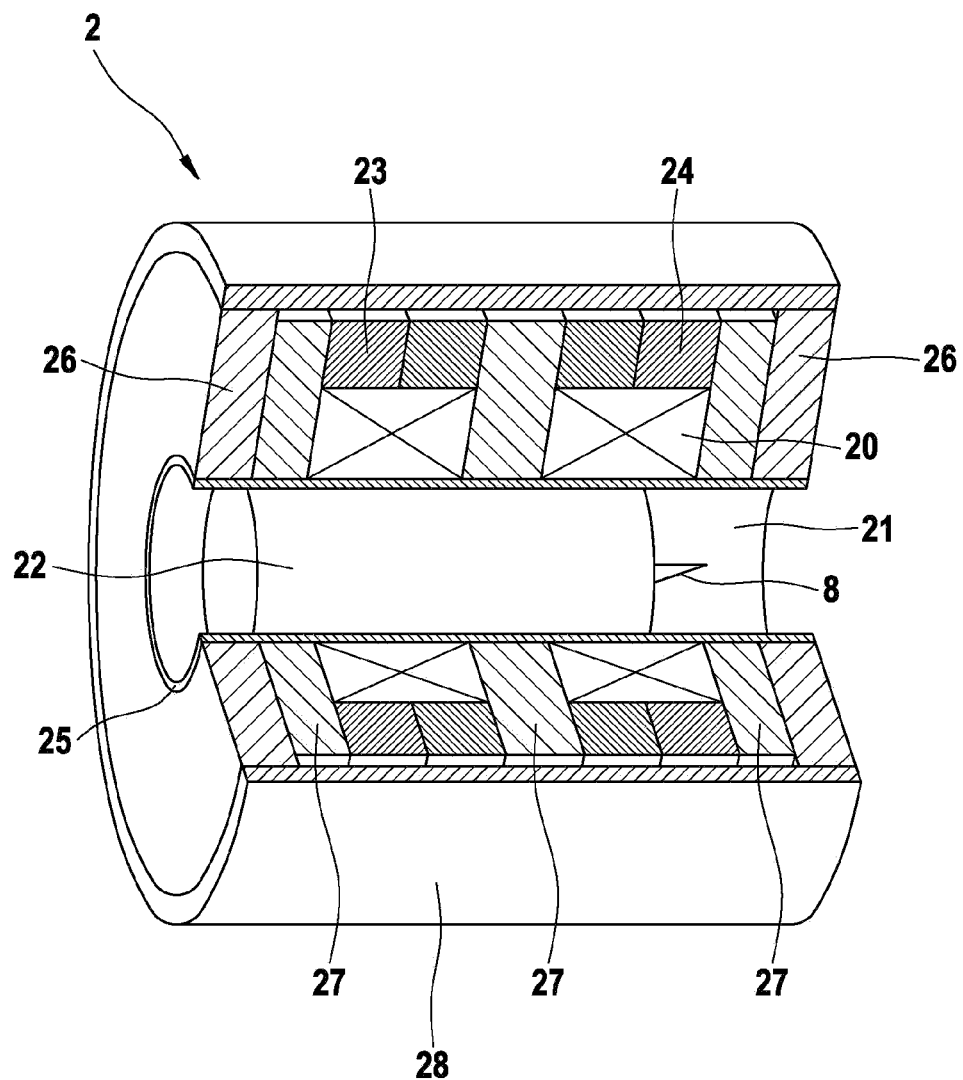
FIG. 4 shows a further exemplary embodiment of a lancet drive of a lancet device according to the present invention in a diagonal view in partial section.

A further exemplary embodiment of a lancet drive 2 for a lancet device is shown in FIG. 4. In the exemplary embodiment shown in FIG. 4, a coil 20 is used as the drive means for generating the drive force, which encloses a drive chamber 21, in which a drive element in the form of a soft-magnetic coil core 22 is movable back and forth to cause a piercing and retraction movement of the lancet by coupling to a lancet, for example, using a pushrod 3 shown in FIGS. 1 through 3. The drive chamber 21 is also enclosed by permanent magnets 23, 24, which are implemented as magnet rings in the exemplary embodiment shown. The permanent magnet rings 23, 24 are ideally situated concentrically to the coil 20.

As the field course of the magnetic field generated by the permanent magnets 23, 24 illustrated in FIG. 5 shows, the permanent magnets 23, 24 are situated with opposite polarity. The permanent magnets 23, 24 thus represent a first and a second magnetic field source, which generate two magnetic fields destructively superimposed in the drive chamber 21. Ideally, the two permanent magnets 23, 24 are identical and are only situated differently. The permanent magnets 23, 24 preferably differ in their strength by less than 30%, especially preferably by less than 20%, particularly by less than 10%.

The permanent magnets 23, 24 work together with the coil 20, which generates a further magnetic field as the third magnetic field source in operation, whose field course is shown in FIG. 6. To trigger a piercing, electric current is caused to flow through the windings of the coil 20, so that the overall magnetic field shown in FIG. 7 results. As may be seen therein, the magnetic field generated by the coil is superimposed constructively in the drive chamber 21 on the magnetic field of the permanent magnet 24 and destructively on the magnetic field of the permanent magnet 23. In this way, an overall field results in the drive chamber 21 which is extensively reduced, ideally canceled out in a first partial area 31 by destructive superposition, and is reinforced, ideally doubled, in a second partial area 32. The two partial areas 31, 32 are ideally equally large.

Before the coil current is turned on, the magnetization direction of the coil core 22 is determined by the permanent magnet 23, so that the coil core 22 is drawn into the first partial area 31 of the drive chamber 21 by the permanent magnet 23, but pushed out of the second partial area 32 of the drive chamber 21 by the oppositely polarized permanent magnet 24. Therefore, the position of the coil core 22 shown in FIG. 5 results before a coil current is turned on.

An increased overall field results in the second partial area 32 of the drive chamber 21 by turning on the coil current, which causes a reversal of the magnetization of the soft-magnetic coil core 22. As a result of this reversal of the magnetization direction of the coil core 22, the coil core 22 is drawn into the second partial area 32 of the drive chamber 21 and thus moved out of the position shown in FIG. 5 into a second position. The stroke of the coil core 22 connected thereto may be used for a piercing movement.

The relationships of the overall field course shown in FIG. 7 may be reversed by a reversal of the direction of the current through the coil 20, so that an increased overall field results in the first partial area 31 of the drive chamber 21 by constructive superposition and a reduced overall field results in the second partial area 32 of the drive chamber 21 by destructive superposition. A change of the overall field of this type causes another change of the magnetization direction of the coil core 22, so that the coil core is retracted into the first partial area 31 of the drive chamber 21 and again reaches the first position.

The length of the coil core 22 is less than the length of the drive chamber 21 enclosed by the first and the second magnetic field sources, i.e., the permanent magnets 23, 24, preferably at least 10% shorter. In this context, only the length of a soft-magnetic part is to be understood as the coil core 22. Possible parts which are attached to a soft-magnetic part, but are not magnetic themselves, such as a pushrod made of plastic, are not to be viewed as the coil core in this regard.

The drive principle described on the basis of FIGS. 4 through 7 may also be used in a corresponding way in that the two permanent magnets 23, 24 are replaced by coils having opposing winding directions and the coil 20 is replaced by a permanent magnet of suitable strength.

In the exemplary embodiment shown in FIG. 4, the coil core 22 is situated in a sliding tube 25. The sliding tube 25 is centered using centering rings 26 in the drive chamber 21 inside the soft-magnetic return path 28, which is formed by an iron tube which encloses the pole shoe 27, the permanent magnets 23, 24, and also the coil 20 and the drive chamber 21. Soft-magnetic pole shoes 27 are placed on the sliding tube 25 and the permanent magnets 23 and 24 are placed having opposite polarization direction between the pole shoes 27.

In the exemplary embodiment described on the basis of FIGS. 4 through 7, the permanent magnet 23 generates a magnetic retention force which is oriented opposite to the drive force generated by the permanent magnet 24 and the coil 20. The coil 20 is both triggering means and also drive means in this exemplary embodiment. Using the coil 20 as the triggering means, the retention force generated by the permanent magnet 23, namely its magnetic field, may be reduced enough that the lancet 8 is accelerated in the direction toward the skin surface under the effect of the drive force generated by the drive means, namely the permanent magnet 24 and the coil 20.

As in the exemplary embodiment described on the basis of FIGS. 1 through 3, in the exemplary embodiment described on the basis of FIGS. 4 through 7, the coil 20 is also connected via a current buffer and/or a voltage converter to an internal current source of the lancet device, such as a battery, so that an intensive current pulse may be generated using commercially available batteries. For the most rapid possible piercing and retraction movement, it is favorable to perform changes of the voltage applied to the coil 20 as rapidly as possible, i.e., to use voltage pulses having a rectangular voltage profile. The voltage supply of the coil 20 therefore delivers voltage pulses having rectangular flanks. Rectangular voltages are especially favorable, because the retraction movement of the lancet may be initiated by the voltage change of a rectangular voltage pulse.

What is claimed is:

1. A lancet device, by which a lancet can be displaced along a piercing path to generate a piercing wound in a skin surface, in particular to obtain bodily fluid for diagnostic purposes, comprising:

a lancet;
a lancet drive having drive means for generating a drive force for a piercing movement of the lancet along the piercing path in the direction toward the skin surface,
the lancet drive comprises a first magnet, by which a magnetic retention force directed opposite to the drive force may be generated,
the lancet drive also comprises triggering means, by which the retention force may be reduced enough that the lancet is accelerated in the direction toward the skin surface under the effect of the drive force generated by the drive means,
the drive means comprises a second magnet which is situated with opposite polarity to the first magnet generating the retention force, wherein the second magnet is a permanent magnet,
wherein the triggering means comprise a coil, by which a magnetic field may be generated, which at least partially, compensates for the retention force of the first magnet, and
wherein the first and second magnets are magnetic rings,
wherein the coil is situated inside the first and second magnets in a fixed position relative to the first and second magnets, and
wherein the lancet drive includes a drive element in the form of a soft-magnetic coil core.

2. The lancet device claim 1, wherein the first magnet is a permanent magnet.

3. The lancet device according to claim 1, wherein the coil is connected to an internal current source of the lancet device via at least one of a current buffer and a voltage converter to generate high-performance current pulses.

4. The lancet device according to claim 1, wherein the soft-magnetic coil core is formed by a permanent magnet or contains the permanent magnet.

5. The lancet device according to claim 4, wherein the coil enclose a drive chamber, in which the coil core is movable, whose movement is transmitted in operation to the lancet as the piercing and retraction movement.

6. The lancet device according to claim 1, wherein the magnetic field generated by the second magnet of the drive means is reinforced by constructive superposition with a further magnetic field, which is generated using a coil current, in a first phase of a piercing movement, in which the lancet is accelerated by the drive force in the direction toward the skin surface.

7. The lancet device according to claim 1, wherein the magnetic field of the coil completely compensates for the retention force of the first magnet.

8. A lancet device, comprising:
a lancet; and
a lancet drive including
a drive chamber,
a drive coil wrapped around the drive chamber,
a soft-magnetic core received in the drive chamber, the soft-magnetic core being coupled to the lancet to actuate the lancet,
a first permanent magnet enclosing the drive chamber, the first permanent magnet generating a retention magnetic field that creates a retention force to retain the soft-magnetic core in the drive chamber at a first position,
a second permanent magnet enclosing the drive chamber, the second permanent magnet generating a drive magnetic field that generates a drive force to drive the soft-magnetic core to a second position, wherein the first permanent magnet and the second permanent magnet are situated with opposite polarities along the drive chamber, wherein the drive coil is situated in a fixed position relative to the first permanent magnet and the second permanent magnet;

wherein the drive coil is configured to reverse the polarity of the soft-magnetic core when a first current is applied to the drive coil to drive the soft-magnetic core from the first position to the second position where the lancet is extended, wherein the drive coil is configured to increase the retention magnetic field generated by the first permanent magnet through constructive superposition and to decrease the drive magnetic field generated by the second magnet through destructive superposition when a second current is applied to the drive coil that is opposite the first current for retracting the soft-magnetic core from the second position to the first position where the lancet is retracted, and wherein the first and second magnets are magnetic rings that surround the drive coil, the drive coil being radially disposed between the soft-magnetic core and the first and second magnets.

9. The lancet device according to claim 8, further comprising:

an internal current source; and a current buffer connecting the coil to the internal current source to generate high-performance current pulses.

10. The lancet device according to claim 9, wherein the internal current source includes a battery.

11. The lancet device according to claim 10, wherein the current buffer includes a capacitor.

12. The lancet device according to claim 10, wherein the current buffer includes a lithium-polymer accumulator.

13. The lancet device according to claim 8, further comprising:

an internal current source; and a voltage converter connecting the coil to the internal current source to generate high-performance current pulses.

14. The lancet device according to claim 13, wherein the voltage converter includes a DC/DC converter.

* * * * *